(12) United States Patent
Iketaki et al.

(10) Patent No.: US 7,351,323 B2
(45) Date of Patent: Apr. 1, 2008

(54) QUANTITATIVE ANALYZING METHOD AND QUANTITATIVE ANALYZER USING SENSOR

(75) Inventors: Kazuo Iketaki, Kyoto (JP); Yoichi Inoue, Kyoto (JP)

(73) Assignee: Arkray, Inc., Kyoto (JP)

( * ) Notice: Subject to any disclaimer, the term of this patent is extended or adjusted under 35 U.S.C. 154(b) by 895 days.

(21) Appl. No.: 10/466,453

(22) PCT Filed: Jan. 15, 2002

(86) PCT No.: PCT/JP02/00204

§ 371 (c)(1), (2), (4) Date: Dec. 2, 2003

(87) PCT Pub. No.: WO02/057768

PCT Pub. Date: Jul. 25, 2002

(65) Prior Publication Data

US 2005/0258034 A1 Nov. 24, 2005

(30) Foreign Application Priority Data

Jan. 17, 2001 (JP) .............................. 2001-008953

(51) Int. Cl.
*G01N 27/327* (2006.01)

(52) U.S. Cl. .............. 205/777.5; 204/401; 204/403.02; 204/406

(58) Field of Classification Search ........... 204/403.01, 204/403.02, 403.1, 406, 401; 205/777.5, 205/792

See application file for complete search history.

(56) References Cited

U.S. PATENT DOCUMENTS 5,243,516 A 9/1993 White
5,352,351 A 10/1994 White et al.
6,576,117 B1 * 6/2003 Iketaki et al. ............ 205/777.5

FOREIGN PATENT DOCUMENTS

| EP | 0 732 406 | 9/1996 |
|---|---|---|
| EP | 1 074 832 | 2/2001 |
| EP | 1 172 649 | 1/2002 |
| JP | 5-502727 | 5/1993 |
| JP | 8-502589 | 3/1996 |
| JP | 11-304748 | 11/1999 |
| JP | 11-326262 | 11/1999 |
| JP | WO 99/60391 A1 * | 11/1999 |
| JP | 2001-208718 | 8/2001 |

* cited by examiner

*Primary Examiner*—Kaj K. Olsen
(74) *Attorney, Agent, or Firm*—Hamre, Schumann, Mueller & Larson, P.C.

(57) ABSTRACT

A quantitative analyzing method is provided for electrochemically measuring the concentration of a substance in a sample liquid using a sensor including a reagent layer (30) which contains a reagent for reacting with the substance and to which (30) the sample liquid is introduced, and a first electrode (22) and a second electrode (23) for applying a voltage to the reagent layer (30). The method includes a current measuring step for applying a voltage across the first electrode (22) and the second electrode (23) for measuring current flowing between the first and the second electrodes (22,23), a parameter calculating step for calculating a parameter based on the measured current, and a determining step for determining a state of the sample liquid introduced to the reagent layer (30) based on the parameter and at least one predetermined constant.

20 Claims, 8 Drawing Sheets

| | Number Determined to be Insufficient (n=25) | |
| --- | --- | --- |
| | When Sufficient Amount Supplied | When Insufficient Amount Supplied |
| Lower Concentration | 0 | 25 |
| Medium Concentration | 0 | 25 |
| Higher Concentration | 0 | 25 |

FIG.10
PRIOR ART

QUANTITATIVE ANALYZING METHOD AND QUANTITATIVE ANALYZER USING SENSOR

TECHNICAL FIELD

The present invention relates to a quantitative analyzing method and a quantitative analyzer for electrochemically measuring the concentration of a substance contained in a sample liquid using a sensor.

BACKGROUND ART

As one means of determining the quantity of a substance contained in a sample liquid, electrochemically measuring the concentration of the substance in the sample liquid using a sensor is known. As the sensor, a sensor of a capillary type is widely used which is so designed that the sample liquid is introduced to a reagent layer by capillary action. Generally, such a capillary sensor includes a capillary having an inlet port. The capillary includes a pair of electrodes and a reagent layer laminated thereon. The reagent layer contains various reagents necessary for a certain reaction system such as a redox chemical substance or oxidoreductase depending on the substance to be measured, i.e. the object of the determination.

In determining the quantity of the substance contained in the sample liquid using such a sensor, the sensor is set to a quantitative analyzer and the sample liquid is supplied to the inlet port of the capillary of the sensor. At that time, the paired electrodes of the sensor are electrically connected to the voltage application means incorporated in the quantitative analyzer. The sample liquid travels within the capillary by capillary action to reach the reagent layer and dissolves the reagent such as a redox agent contained in the reagent layer. Part of the reagent reacts specifically with the substance in the sample liquid. Thereafter, when the quantitative analyzer applies a predetermined voltage to the reagent layer, a current corresponding to the concentration of the substance flows between the paired electrodes. The quantitative analyzer measures the current. The concentration of the substance is determined based on the measured current and a calibration curve or a calibration-equation prepared in advance.

For example, for measuring the glucose concentration in blood, use is made of a biosensor provided with a reagent layer containing glucose oxidase and potassium ferricyanide. When the blood is introduced to the reagent layer, glucose oxidase oxidizes glucose to gain an electron, whereas potassium ferricyanide receives the electron from glucose oxidase to be reduced to potassium ferrocyanide. Thus, when a predetermined voltage is applied across the paired electrodes, a current corresponding to the concentration of potassium ferrocyanide flows between the electrodes. Since the potassium ferrocyanide concentration corresponds to the glucose concentration in the blood, the glucose concentration in blood is determined by measuring the current.

Figure 10:
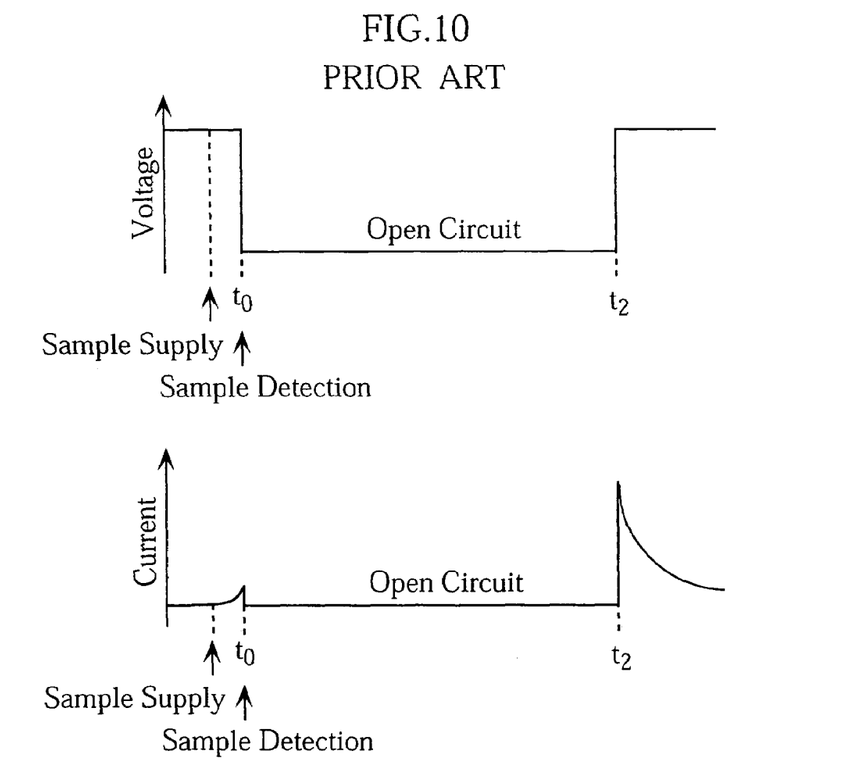
FIG. 10 shows variation with time of the voltage applied and variation with time of measured current in a prior art quantitative analyzer.

As a prior art quantitative analyzer for electrochemically measuring the concentration of a substance in a sample liquid using a sensor, an automatic quantitative analyzer is known which uses a disposable sensor and utilizes a potential step method. Generally, such an automatic quantitative analyzer is designed to automatically start the measurement operation when a sample liquid is introduced to the reagent layer. Specifically, when a sensor is set to the quantitative analyzer, a predetermined voltage is applied to a pair of electrodes of the sensor, as shown in FIG. 10. When the sample liquid is introduced to the inlet port of the capillary, the sample liquid is guided to the reagent layer by capillary action, thereby changing the current flowing between the electrodes. Based on the change in the current, the quantitative analyzer detects the introduction of the sample liquid to the reagent layer and intermits the application of voltage across the electrodes (time $t_0$). After the lapse of a predetermined period, the automatic quantitative analyzer restarts the application of voltage across the electrodes (time $t_2$) and measures the current flowing between the electrodes. Subsequently, the automatic quantitative analyzer determines the concentration of the substance based on the measurements and a table prepared based on a calibration curve or a calibration equation, for example.

However, in such a prior art quantitative analyzer, the current flowing between the paired electrodes is utilized only for determining whether or not the sample liquid is introduced to the reagent layer, and the measurement is started without considering the amount of the sample liquid introduced to the reagent layer. Therefore, in the prior art automatic quantitative analyzer, the concentration of the substance may be determined erroneously due to the insufficiency in the amount of the sample liquid.

For example, in the case where the sample liquid is blood, even when a suitable amount of blood is supplied to the sensor, the amount of blood reaching the reagent layer by capillary action may be in sufficient due to the high hematocrit or viscosity. When the amount of blood introduced to the sensor is insufficient, the amount of blood reaching the reagent layer is accordingly insufficient even if the hematocrit or viscosity is not so high. In such cases, the prior art automatic quantitative analyzer produces measurement results including an unacceptable level of error in the measuring of the glucose concentration in the blood.

JP-A-8-502589 discloses a method and an apparatus for determining whether or not the amount of a sample liquid supplied to a test cell is sufficient by setting two threshold values with respect to a current flowing through a reaction region in the test cell. In this prior art, the first threshold value is set in advance for detecting the introduction of the sample liquid to the reaction region, whereas the second threshold value, which is greater than the first one, is set in advance for determining whether or not the amount of the sample liquid is sufficient for continuing the measurement.

JP-A-8-502589 further discloses a method and an apparatus for determining, with respect to a current flowing through the reaction region depending on the concentration of the substance to be measured, whether or not a measured current value follows the cottrell equation. This prior art method calculates the ratio of the sum of current values at a plurality of points of time after starting the measurement to one of the current values.

Similarly, JP-A-5-502727 discloses a method for determining, with respect to a current flowing through the reaction region depending on the concentration of the substance to be measured, whether or not a measured current value follows the cottrell equation. This prior art method calculates the ratio between current values at two different points of time after starting the measurement.

The present invention is conceived under such circumstances, and an object of the invention is to provide a quantitative analyzing method and a quantitative analyzer capable of determining the state of a sample liquid, particularly the sufficiency or insufficiency of the amount of the sample liquid introduced to a reagent layer of a sensor based on a measured current which depends on the concentration of the substance to be measured even when the current does not follow the cottrell equation.

DISCLOSURE OF THE INVENTION

According to a first aspect of the present invention, there is provided a quantitative analyzing method for electrochemically measuring concentration of a substance in a sample liquid using a sensor including a reagent layer which contains a reagent for reacting with the substance and to which the sample liquid is introduced, and a first and a second electrodes for applying a voltage to the reagent layer. The method includes a current measuring step for applying a voltage across the first electrode and the second electrode for measuring current flowing between the first electrode and the second electrode, a parameter calculating step for calculating a parameter based on the measured current, and a determining step for determining a state of the sample liquid introduced to the reagent layer based on the parameter and at least one predetermined constant.

According to a second aspect of the present invention, there is provided a quantitative analyzing method for electrochemically measuring concentration of a substance in a sample liquid using a sensor including a reagent layer which contains a reagent for reacting with the substance and to which the sample liquid is introduced, and a first and a second electrodes for applying a voltage to the reagent layer. The method includes a current measuring step for applying a voltage across the first electrode and the second electrode for measuring current flowing between the first electrode and the second electrode, a parameter calculating step for calculating a parameter based on the measured current, and a determining step for determining whether or not the sample liquid introduced to the reagent layer is insufficient in amount based on the parameter and at least one predetermined constant.

Preferably, the parameter includes a current value of the current flowing between the first electrode and the second electrode at a predetermined point of time. Preferably, the parameter includes a difference between a first current value at a first predetermined point of time and a second current value at a second predetermined point of time of the current flowing between the first electrode and the second electrode. Preferably, the parameter includes a differentiation of the current flowing between the first electrode and the second electrode at a predetermined point of time. Preferably, the parameter includes a third difference between a first value and a second value with respect to the current flowing between the first electrode and the second electrode, the first value being obtained by dividing a current value at a third predetermined point of time by a first difference between a current value at a first predetermined point of time and a current value at a second predetermined point of time, the third point of time being included in a period between the first point of time and the second point of time, the second value being obtained by dividing a current value at a sixth predetermined point of time by a second difference between a current value at a fourth predetermined point of time and a current value at a fifth predetermined point of time, the sixth point of time being included in a period between the fourth point of time and the fifth point of time.

Preferably, a series of process steps including the current measuring step, the parameter calculating step and the determining step is repeated a plurality of times, and the sample liquid introduced to the reagent layer is finally determined to be insufficient in amount when the sample liquid is determined to be insufficient in every determining step.

Preferably, the current measuring step is continued for a first period from before to after a point of time when the introduction of the sample liquid to the reagent layer is detected based on the current flowing between the first electrode and the second electrode, and at least a part of the parameter is calculated based on the current measured in the first period.

Preferably, the series of process steps including the current measuring step, the parameter calculating step and the determining step is repeated a predetermined number of times after the sample liquid is introduced to the reagent layer and before and/or after a second period during which current is not substantially caused to flow between the first electrode and the second electrode.

Preferably, at least part of said at least one constant is varied depending on a temperature of the sample liquid.

According to a third aspect of the present invention, there is provided a quantitative analyzer for electrochemically measuring concentration of a substance in a sample liquid using a sensor including a reagent layer which contains a reagent for reacting with the substance and to which the sample liquid is introduced, and a first and a second electrodes for applying a voltage to the reagent layer. The analyzer comprises voltage applying means for applying a voltage across the first electrode and the second electrode, current measuring means for measuring current flowing between the first electrode and the second electrode, calculating means for calculating a parameter based on the measurement obtained by the current measuring means, and determining means for determining a state of the sample liquid introduced to the reagent layer based on the parameter obtained by the calculating means and at least one predetermined constant.

According to a fourth aspect of the present invention, there is provided a quantitative analyzer for electrochemically measuring concentration of a substance in a sample liquid using a sensor including a reagent layer which contains a reagent for reacting with the substance and to which the sample liquid is introduced, and a first and a second electrodes for applying a voltage to the reagent layer. The analyzer comprises voltage applying means for applying a voltage across the first electrode and the second electrode, current measuring means for measuring current flowing between the first electrode and the second electrode, calculating means for calculating a parameter based on the measurement obtained by the current measuring means, and determining means for determining whether or not the sample liquid introduced to the reagent layer is insufficient in amount based on the parameter calculated by the calculating means and at least one predetermined constant.

Preferably, the calculating means calculates a current value of the current flowing between the first electrode and the second electrode at a predetermined point of time as at least a part of the parameter. Preferably, the calculating means calculates a difference between a current value at a first predetermined point of time and a current value at a second predetermined point of time of the current flowing between the first electrode and the second electrode as at least a part of the parameter. Preferably, the calculating means calculates a differentiation of the current flowing between the first electrode and the second electrode at a predetermined point of time as at least a part of the parameter. Preferably, the calculating means calculates, as at least a part of the parameter, a third difference between a first value and a second value with respect to the current flowing between the first electrode and the second electrode, the first value being obtained by dividing a current value at a third predetermined point of time by a first difference between a current value at a first predetermined point of time and a current value at a second predetermined point of time, the third point of time being included in a period between the first point of time and the second point of time, the second value being obtained by dividing a current value at a sixth predetermined point of time by a second difference between a current value at a fourth predetermined point of time and a current value at a fifth predetermined point of time, the sixth point of time being included in a period between the fourth point of time and the fifth point of time.

Preferably, a combination of operations performed by the current measuring means, the calculating means and the determining means is performed a plurality of times, and the sample liquid introduced to the reagent layer is finally determined to be insufficient in amount when the determining means determines that the sample liquid is insufficient at every repetition of the combined operations.

Preferably, the current measuring means operates for a first period from before to after a point of time when the introduction of the sample liquid to the reagent layer is detected based on the current flowing between the first electrode and the second electrode, and the calculating means calculates at least a part of the parameter based on the current measured in the first period.

Preferably, a combination of operations performed by the current measuring means, the calculating means and the determining means is repeated an optional number of times after the sample liquid is introduced to the reagent layer and before and/or after a second period during which current is not substantially caused to flow between the first electrode and the second electrode.

Preferably, the determining means varies at least part of said at least one constant depending on a temperature of the sample liquid.

According to a fifth aspect of the present invention, there is provided a quantitative analyzing method for electrochemically measuring concentration of a substance in a sample liquid using a sensor including a reagent layer which contains a reagent for reacting with the substance and to which the sample liquid is introduced, and a first and a second electrodes for applying a voltage to the reagent layer. The method includes a first current measuring step for applying a voltage across the first electrode and the second electrode for a first period for measuring current flowing between the first electrode and the second electrode, a sample liquid introducing step for introducing the sample liquid to the reagent layer within the first period, a first parameter calculating step for calculating a parameter based on the current measured in the first current measuring step, a first determining step for determining whether or not the sample liquid introduced to the reagent layer is insufficient in amount based on the parameter obtained in the first parameter calculating step and at least one first constant determined in advance, a reaction promoting step for substantially intermitting voltage application across the first electrode and the second electrode for a second period, a second current measuring step for applying a voltage across the first electrode and the second electrode for a third period for measuring current flowing between the first electrode and the second electrode, a second parameter calculating step for calculating a parameter based on the current measured in the second current measuring step, and a second determining step for determining whether or not the sample liquid introduced to the reagent layer is insufficient in amount based on the parameter obtained in the second parameter calculating step and at least one second constant determined in advance.

Preferably, a first series of process steps including the first current measuring step, the first parameter calculating step and the first determining step and/or a second series of process steps including the second current measuring step, the second parameter calculating step and the second determining step are performed respectively a plurality of times. The sample liquid introduced to the reagent layer is finally determined to be insufficient in amount when the sample liquid is determined to be insufficient in every first determining step in the first series of process steps or in every second determining step in the second series of process steps.

BEST MODE FOR CARRYING OUT THE INVENTION

Preferred embodiments of the present invention will be described below in detail with reference to the accompanying drawings.

Figure 1:
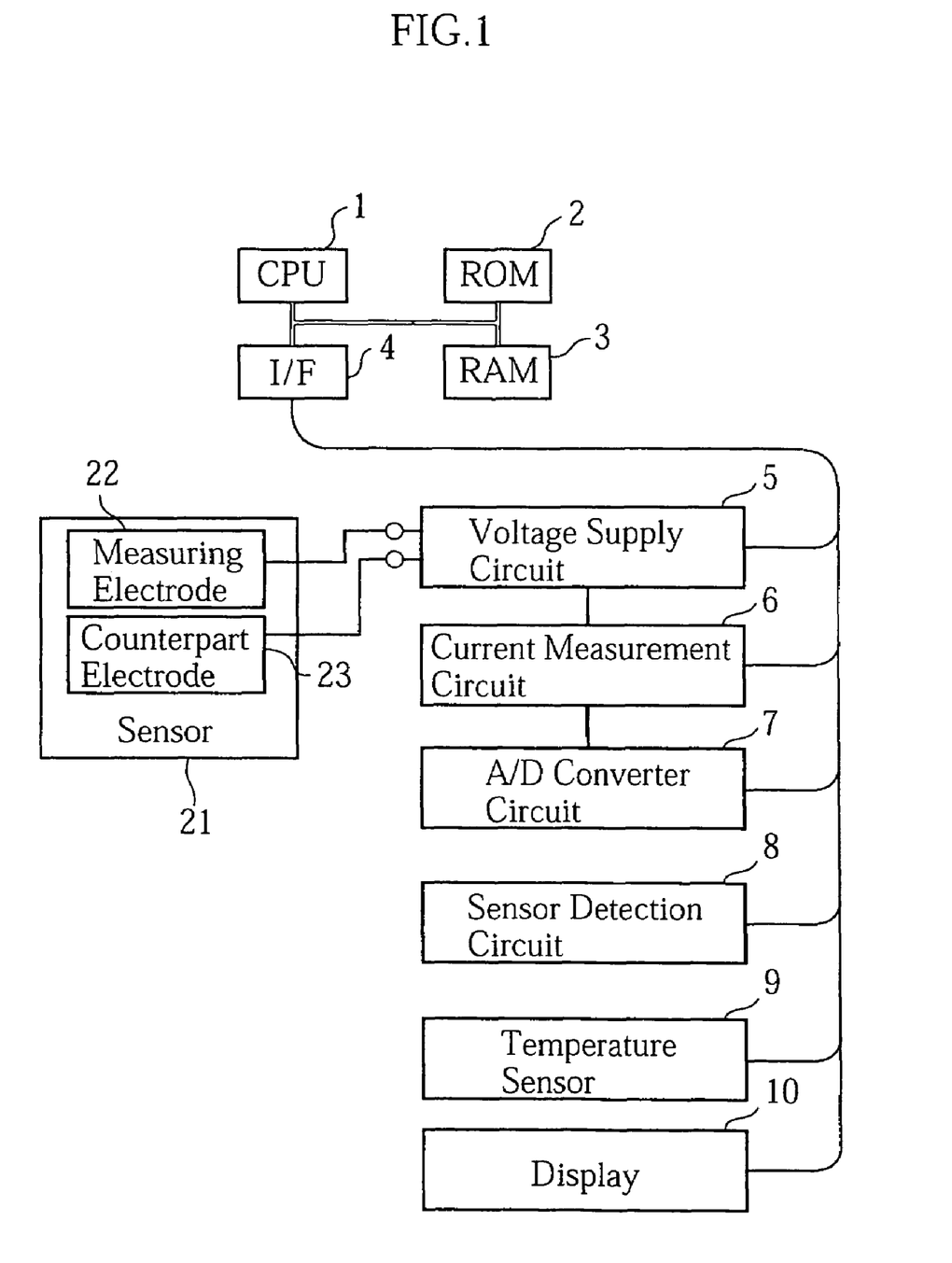
FIG. 1 is a schematic circuit block diagram of a quantitative analyzer using a sensor according to the present invention.

FIG. 1 is a schematic circuit block diagram of a quantitative analyzer using a sensor according to the present invention. In this embodiment, the quantitative analyzer is used for measuring the glucose concentration in blood. Therefore, the sensor 21 used in this embodiment is classified as a biosensor. The quantitative analyzer includes a CPU (central processing unit) 1, a ROM (read only memory) 2, a RAM (random access memory) 3, an interface circuit 4, a voltage supply circuit 5, a current measurement circuit 6, an analog/digital converter circuit 7, a sensor detection circuit 8, a temperature sensor 9 and a display 10. The CPU 1, the ROM 2, the RAM 3 and the interface circuit 4 are connected to each other through bus lines. The voltage supply circuit 5, the current measurement circuit 6, the analog/digital converter circuit 7, the sensor detection circuit 8, the temperature sensor 9 and the display 10 are connected to the interface circuit 4. The voltage supply circuit 5 has a pair of output terminals to which a measuring electrode 22 and a counter electrode 23 of the sensor 21 are connected when the sensor 21 is mounted to the quantitative analyzer.

The CPU 1 controls the entire quantitative analyzer. The ROM 2 stores a program or data for operating the CPU 1. The RAM 3 provides the CPU 1 with a working area and stores various kinds of data. The interface circuit 4 controls the communication of the CPU 1 with the voltage supply circuit 5, the current measurement circuit 6, the analog/digital converter circuit 7, the sensor detection circuit 8, the temperature sensor 9 and the display 10. The voltage supply circuit 5 applies a predetermined voltage across the measuring electrode 22 and the counterpart electrode 23 of the sensor 21 under the control of the CPU 1. The current measurement circuit 6 measures the current flowing between the measuring electrode 22 and the counterpart electrode 23, i.e. the current supplied from the voltage supply circuit 5 to the sensor 21, and outputs a voltage corresponding to the measurement. The analog/digital converter circuit 7 converts an analog voltage from the current measurement circuit 6 to digital data for supplying to the interface circuit 4. The sensor detection circuit 8 detects that the sensor 21 has properly mounted to the quantitative analyzer and supplies a detection signal to the CPU 1 via the interface circuit 4. The temperature sensor 9 detects the ambient temperature of the quantitative analyzer or the temperature of a sample liquid and supplies a detection signal to the CPU 1 via the interface circuit 4. The display 10 displays various information such as a measurement of glucose concentration or an alarm for notifying the insufficiency in blood amount on a display surface under the control of the CPU 1.

Figure 2:
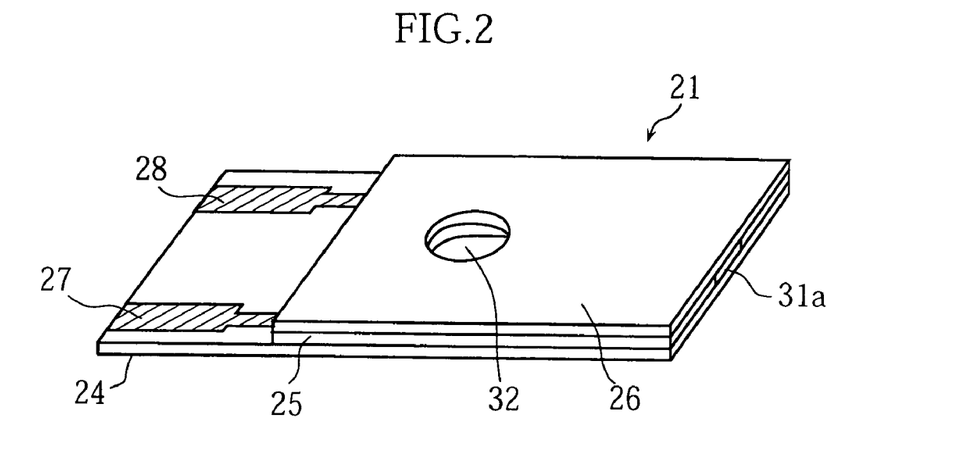
FIG. 2 is a perspective view of the sensor.
Figure 3:
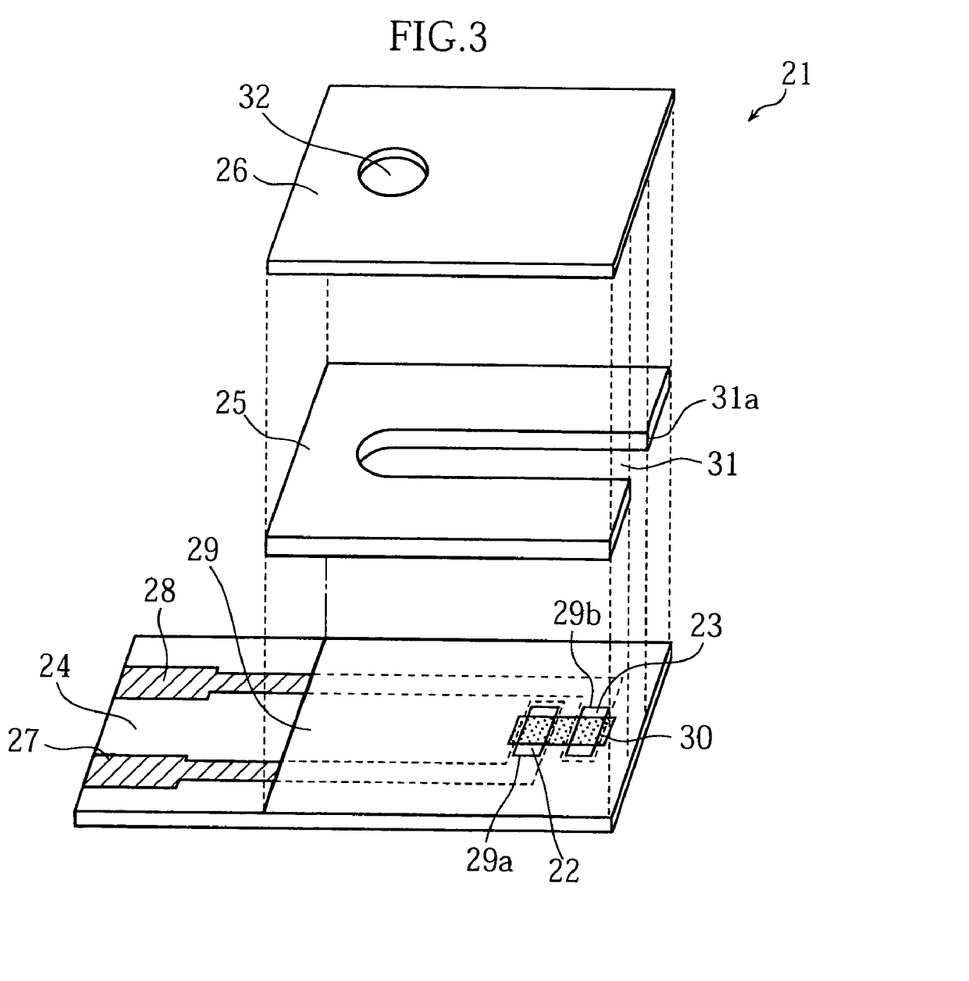
FIG. 3 is an exploded perspective view of the sensor shown in FIG. 2.

FIG. 2 is a perspective view of the sensor 21. FIG. 3 is an exploded perspective view of the sensor 21. The sensor 21 has a laminated structure comprising a substrate 24, a spacer 25 and a cover 26. The substrate 24 has a tip end on the right-hand side of the figures and a base end on the opposite side. Each of the spacer 25 and the cover 26 has a configuration coinciding with the substrate 24 at the tip end and is laminated on the substrate 24 while exposing the base end of the substrate 24.

The measuring electrode 22 and the counterpart electrode 23 arranged parallel to each other are provided adjacent to the tip end of the substrate 24. The measuring electrode 22 is connected to one end of a conductor 27. The other end of the conductor 27 extends up to the base end of the substrate 24 for exposure to the outside. A thin insulating layer 29 is formed between the substrate 24 and the spacer 25. The insulating layer 29 is formed with an opening 29a for partially exposing the measuring electrode 22 and an opening 29b for partially exposing the counterpart electrode 23. The substrate 24 is provided with a reagent layer 30 bridging the measuring electrode 22 and the counterpart electrode 23 from above the insulating layer 29. The reagent layer 30 contains glucose oxidase and potassium ferricyanide. In FIG. 3, the reagent layer 30 is illustrated as transparent for showing the portion below the reagent layer 30.

The spacer 25 is formed with a slit extending from the tip end on the right-hand side of the figure toward the other hand. Between the substrate 24 and the cover 26, the slit defines a capillary 31 and an inlet port 31a for introducing blood as a sample liquid to the reagent layer 30 by capillary action. The cover 26 is formed with an air vent 32. The capillary 31 is in communication with the atmosphere through the air vent 32.

Figure 4:
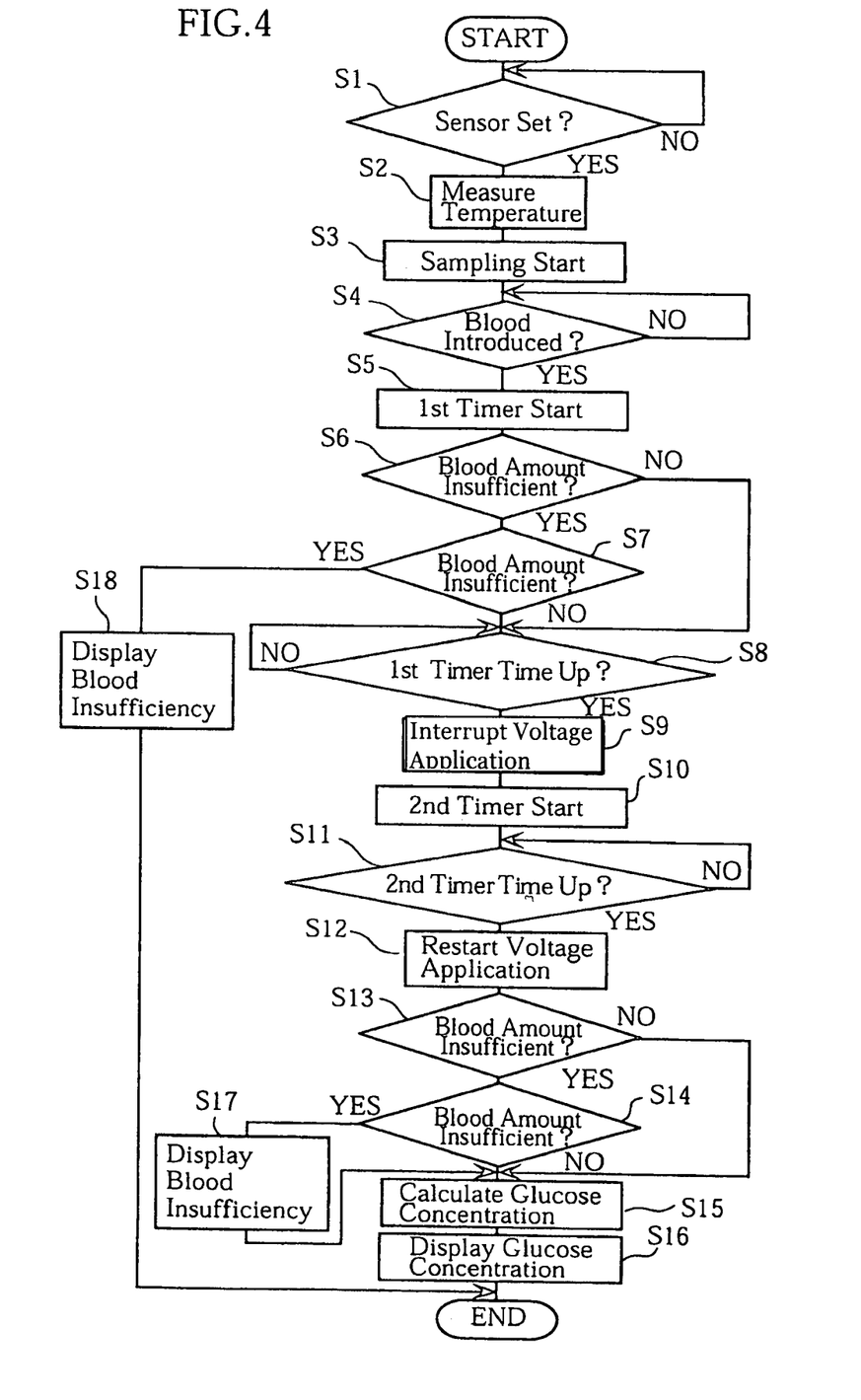
FIG. 4 is a flowchart of the analyzing operation by the quantitative analyzer shown in FIG. 1.
Figure 5:
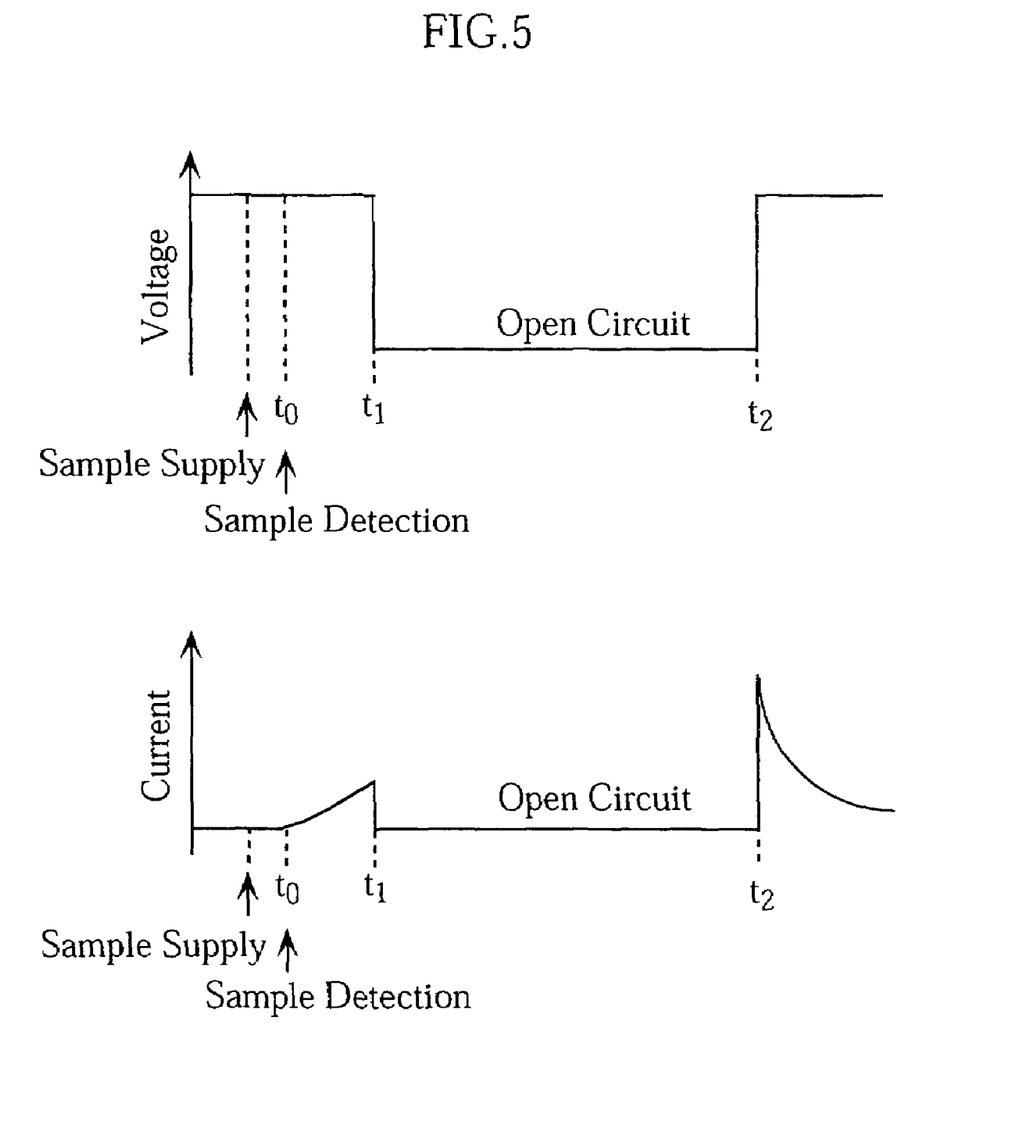
FIG. 5 shows variation with time of the voltage applied across a measuring electrode and a counterpart electrode and variation with time of a current flowing between the measuring electrode and the counterpart electrode.

FIG. 4 is a flowchart of the analyzing operation by the quantitative analyzer shown in FIG. 1. FIG. 5 shows the variation with time of the voltage applied across the measuring electrode 22 and the counterpart electrode 23 and the variation with time of the current flowing between the measuring electrode 22 and the counter part electrode 23 in accordance with the applied voltage in the analyzing operation.

In Step S1, the CPU 1 determines whether or not the sensor 21 is properly set to the quantitative analyzer. Specifically, when the sensor 21 is properly set to the quantitative analyzer, the sensor detection circuit 8 detects the setting and supplies a detection signal to the CPU 1 via the interface circuit 4. Upon receiving the detection signal, the CPU 1, which is checking the supply of a detection signal from the sensor detection circuit 8, determines that the sensor 21 is properly set.

When the sensor 21 is properly set (S1:YES), the CPU 1 measures the temperature of the reagent layer 30 in Step S2. Specifically, the CPU 1 checks the ambient temperature of the quantitative analyzer based on a detection signal from the temperature sensor 9 and stores the temperature in the RAM 3. If the sensor 21 is not properly set in Step S1 (S1:NO), Step S1 is repeated until the sensor 21 is properly set.

Subsequently, in Step S3, the CPU 1 starts sampling. Specifically, the CPU 1 controls the voltage supply circuit 5 to apply a predetermined voltage across the measuring electrode 22 and the counterpart electrode 23. The voltage may be 500 mV, for example. During the voltage application, the current measurement circuit 6 continues to measure the current flowing between the measuring electrode 22 and the counterpart electrode 23 and supplies a voltage corresponding to the measured current to the analog/digital converter circuit 7. The voltage from the current measurement circuit 6 is sampled by the analog/digital converter circuit 7 at a predetermined sampling frequency for conversion into current data. The CPU 1 takes the current data from the analog/digital converter circuit 7 at predetermined time intervals and stores the data in the RAM 3.

Subsequently, in Step S4, the CPU 1 determines whether or not blood is introduced to the reagent layer 30. Specifically, based on the current data from the analog/digital converter circuit 7, the CPU 1 checks whether or not the current flowing between the measuring electrode 22 and the counterpart electrode 23 has reached a predetermined threshold value. When the blood is introduced to the reagent layer, the current flowing between the measuring electrode 22 and the counter part electrode 23 changes due to the reaction at the reagent layer 30. The CPU 1 checks this change.

If the blood is introduced to the reagent layer 30 (S4: YES), the CPU 1 starts a first timer in Step S5. As shown in FIG. 5, the first timer is a timer for continuing voltage application across the measuring electrode 22 and the counterpart electrode 23 for a time period from time $t_0$ to time $t_1$. The time $t_0$ indicates the point of time when the blood is introduced to the reagent layer 30. In this embodiment, the time period from time $t_0$ to time $t_1$ may be one second, for example. Though not illustrated, such a timer is realized by a counter which counts clock signals of a predetermined frequency. If the blood is not introduced to the reagent layer 30 in Step 4 (S4:NO), Step S4 is repeated until the blood is introduced to the reagent layer 30.

In the subsequent Step S6, the CPU 1 determines whether or not the amount of blood introduced to the reagent layer 30 is insufficient. Specifically, the CPU 1 searches the electric current data stored in the RAM 3 and determines whether or not the blood amount is insufficient based on the following formula (1). In the formula (1), I(0.0) is the current data i.e. the current value at the time $t_0$, I(−0.2) is the current data 0.2 second before the time $t_0$, and a and b are constants experimentally determined and stored in the ROM 2 in advance. The ROM 2 stores values of the constant b associated with the temperatures as a table. The CPU 1 reads the temperature data detected by the temperature sensor 9 from the RAM 3 and reads the constant b from the table of the ROM 2 based on the temperature data. That is, an appropriate constant b is selectively used depending on the temperature variation. If the following formula (1) holds true, the CPU 1 determines that the amount of blood introduced to the reagent layer 30 is insufficient.

$$I(0.0) - aI(-0.2) \leq b \tag{1}$$

If it is determined that the blood amount is insufficient in Step S6 (S6:YES), the CPU 1 determines again, in Step S7, whether or not the amount of blood introduced to the reagent layer 30 is insufficient. This second determination is performed because the current flowing between the measuring electrode 22 and the counter part electrode 23 is weak and unstable around the time $t_0$. The reliability of determination is ensured by the second determination which is performed by continuing voltage application across the measuring electrode 22 and the counterpart electrode 23 and continuing the current measurement after the time $t_0$. Specifically, the CPU 1 searches the current data stored in the RAM 3 and determines whether or not the blood amount is insufficient based on the following formula (2). In the formula (2), I(0.0) is the current data at the time $t_0$, whereas I(0.2) is the current data 0.2 second after the time $t_0$. Thus, the calculation of the formula (2) is performed after the current data 0.2 second after the time $t_0$ is obtained. The values c and d are constants experimentally determined and stored in the ROM 2 in advance. The ROM 2 stores values of the constant d associated with the temperatures as a table. The CPU 1 reads the temperature data detected by the temperature sensor 9 from the RAM 3 and reads the constant d from the table of the ROM 2 based on the temperature data. That is, an appropriate constant d is selectively used depending on the temperature variation. If the following formula (2) holds true, the CPU 1 determines that the amount of blood introduced to the reagent layer 30 is insufficient.

$$I(0.2) - cI(0.0) \leq d \tag{2}$$

If it is determined that the blood amount is not insufficient in Step S7 (S7:NO), the CPU 1 determines, in Step S8, whether or not the time of the first timer is up. In this embodiment, the CPU 1 checks whether one second has passed from the time $t_0$ to reach the time $t_1$. If the time of the first timer is not up in Step S8 (S8:NO), Step 8 is repeated until the time of the first timer is up. If the time of the first timer is up (S8:YES), the CPU 1 controls the voltage supply circuit 5 to intermit the application of voltage across the measuring electrode 22 and the counterpart electrode 23.

If it is determined that the blood amount is not insufficient in Step S6 (S6:NO), Step S8 is performed without performing Step S7. If it is determined that the blood amount is insufficient in Step S7 (S7:YES), the CPU 1 displays a warning to notify the insufficiency of blood amount at the display surface of the display 10 in Step S18 and terminates the process. In the case where the amount of blood introduced to the reagent layer 30 is determined to be insufficient in Step S7, the measurement of the glucose concentration is not performed. This leads to time saving, because the glucose concentration cannot be accurately measured due to the insufficiency of the blood amount. The warning notifying the insufficiency of blood amount is displayed in Step S18 only when the blood amount is determined to be insufficient in both of Step S6 and Step S7.

After the voltage application is intermitted in Step S9, the CPU 1 starts a second timer in Step S10. As shown in FIG. 5, the first timer is a timer for continuing the intermission of the voltage application for a time period from time $t_1$ to time $t_2$. In this embodiment, the time period from time $t_1$ to time $t_2$ may be 24 seconds, for example, and hence, the time period from time $t_0$ to time $t_2$ may be 25 seconds. Though not illustrated, the second timer is realized by a counter which counts clock signals of a predetermined frequency. In the time period of 24 seconds during which the application of voltage across the measuring electrode 22 and the counterpart electrode 23 is intermitted, chemical reaction proceeds at the reagent layer 30. As a result, when the time of the second timer is up, the preparation for electrochemically measuring the glucose concentration in the blood has been completed.

In the subsequent Step S11, the CPU 1 determines whether or not the time of the second timer is up. In this embodiment, the CPU 1 checks whether 24 seconds has passed from the time $t_1$ to reach the time $t_2$. If the time of the second timer is not up in Step S11 (S11:NO), Step 11 is repeated until the time of the second timer is up. If the time of the second timer is up (S11:YES), the CPU 1 controls the voltage supply circuit 5 to restart the application of voltage across the measuring electrode 22 and the counterpart electrode 23 in Step S12.

Next, in Step S13, the CPU 1 determines whether or not the amount of blood introduced to the reagent layer 30 is insufficient. Specifically, the CPU 1 searches the current data stored in the RAM 3 and determines whether or not the blood amount is insufficient based on the formula (3). In the formula (3), I(25.5) is the current data 25.5 seconds after the time $t_0$. The value ΔI(25.5) is a value obtained by subtracting the current data 26.0 seconds after the time $t_0$ from the current data 25.5 seconds after the time $t_0$. The value I(27.5) is the current data 27.5 seconds after the time $t_0$. The value ΔI (27.5) is a value obtained by subtracting the current data 28.0 seconds after the time $t_0$ from the current data 27.5 seconds after the time $t_0$. Thus, the calculation of the formula (3) is performed after the current data 28.0 seconds after the time $t_0$ is obtained. The values e and f are constants experimentally determined and stored in the ROM 2 in advance. The ROM 2 stores values of the constant f associated with the temperatures as a table. The CPU 1 reads the temperature data detected by the temperature sensor 9 from the RAM 3 and reads the constant f from the table of the ROM 2 based on the temperature data. That is, an appropriate constant f is selectively used depending on the temperature variation. If the formula (3) holds true, the CPU 1 determines that the amount of blood introduced to the reagent layer 30 is insufficient.

$$\frac{I(27.5)}{\Delta I(27.5)} - e \cdot \frac{I(25.5)}{\Delta I(25.5)} \leq f \tag{3}$$

If it is determined that the blood amount is insufficient in Step S13 (S13:YES), the CPU 1 determines again whether or not the amount of blood introduced to the reagent layer 30 is insufficient in Step S14. This second determination is performed to prevent the blood amount from being erroneously determined to be insufficient though it is in fact sufficient. Specifically, the CPU 1 searches the current data stored in the RAM 3 and determines whether or not the blood amount is insufficient based on the following formula (4). In the formula (4), I(27.5) is the current data 27.5 seconds after the time $t_0$. The value ΔI (27.5) is a value obtained by subtracting the current data 28.0 seconds after the time $t_0$ from the current data 27.5 seconds after the time $t_0$. The value I(29.5) is the current data 29.5 seconds after the time $t_0$. The value ΔI (29.5) is a value obtained by subtracting the current data 30.0 seconds after the time $t_0$ from the current data 29.5 seconds after the time $t_0$. Therefore, the calculation of the formula (4) is performed after the current data 30.0 seconds after the time $t_0$ is obtained. The values g and h are constants experimentally determined and stored in the ROM 2 in advance. The ROM 2 stores values of the constant h associated with the temperatures as a table. The CPU 1 reads the temperature data detected by the temperature sensor 9 from the RAM 3 and reads the constant h from the table of the ROM 2 based on the temperature data. That is, an appropriate constant h is selectively used depending on the temperature variation. If the formula (4) holds true, the CPU 1 determines that the amount of blood introduced to the reagent layer 30 is insufficient.

$$\frac{I(29.5)}{\Delta I(29.5)} - g \cdot \frac{I(27.5)}{\Delta I(27.5)} \le h \quad (4)$$

If it is determined that the blood amount is not insufficient in Step S14 (S14:NO), the CPU 1 calculates the glucose concentration in the blood introduced to the reagent layer 30 based on the electric current data stored in the RAM 3. The current data used at that time may be the current data 30 seconds after the time $t_0$. In the calculation, reference is made to a calibration curve, a calibration equation, or a table prepared using these. Since the calculation is performed similarly to that in a conventional quantitative analyzer, detailed description thereof is omitted.

If it is determined that the blood amount is not insufficient in Step S13 (S13:NO), Step S15 is performed without performing Step S14. If it is determined that the blood amount is insufficient in Step S14 (S14:YES), the CPU 1 displays a warning to notify the insufficiency of blood amount at the display surface of the display 10 in Step S17 and proceeds to Step S15. The warning notifying the insufficiency of blood amount is displayed in Step S17 only when the amount of blood introduced to the reagent layer 30 is determined to be insufficient in both of Step S13 and Step S14.

In the subsequent Step S16, the CPU 1 displays the glucose concentration obtained by the calculation at the display surface of the display 10 and terminates the process. At that time, the application of voltage across the measuring electrode 22 and the counterpart electrode 23 has been stopped. In the case where the blood amount is determined to be insufficient in both of Step S13 and Step S14, a warning to that effect is displayed together with the glucose concentration in Step S17.

Figure 6:
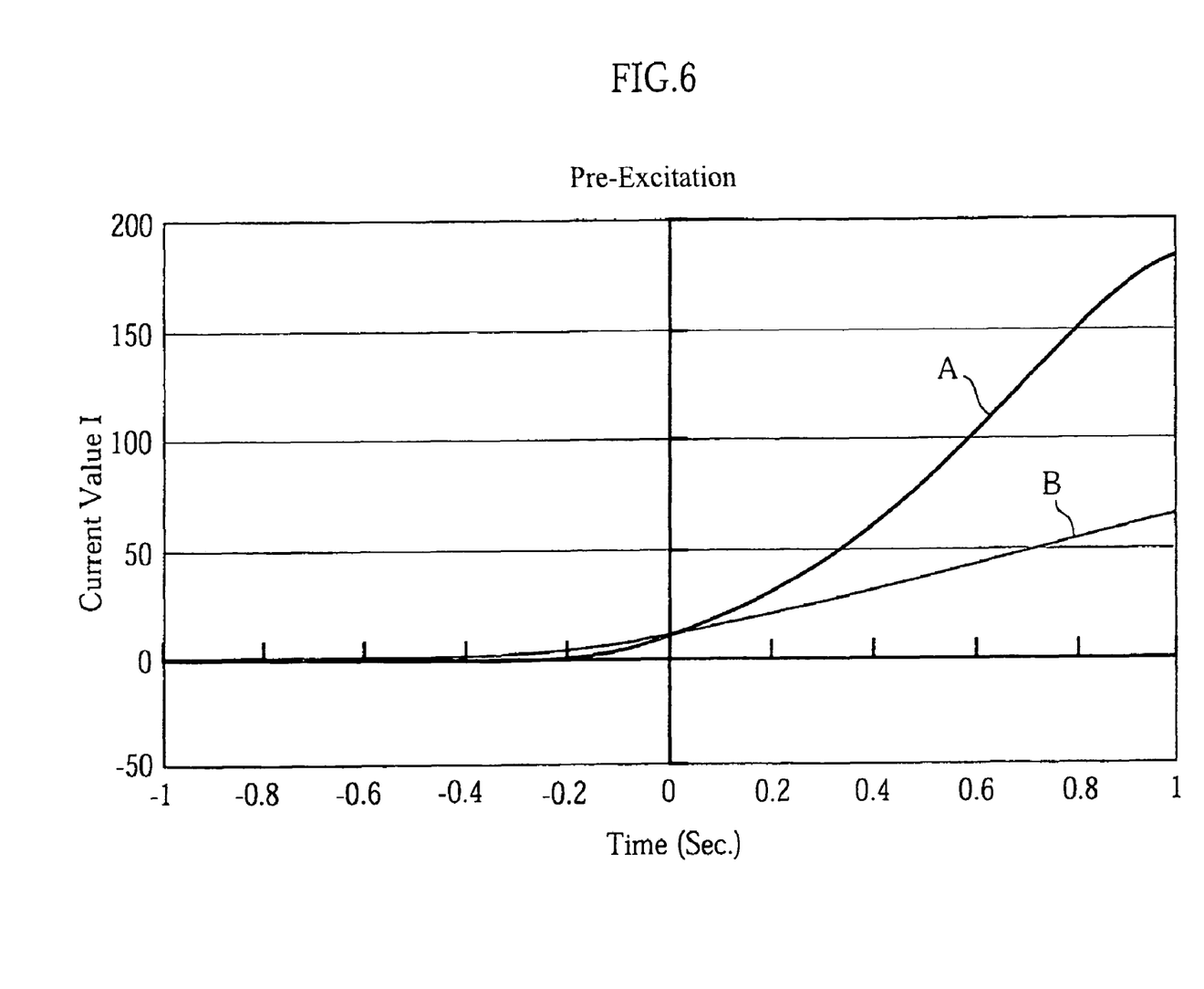
FIG. 6 shows variation with time of the current flowing between the measuring electrode and the counterpart electrode before the application of voltage across the measuring electrode and the counterpart electrode is stopped.

FIG. 6 shows the variation with time of the current flowing between the measuring electrode 22 and the counterpart electrode 23 before the application of voltage across the measuring electrode 22 and the counterpart electrode 23 is intermitted in Step S9. In FIG. 6, the abscissa represents time and the ordinate represents values of current flowing between the measuring electrode 22 and the counterpart electrode 23. The point 0 in the abscissa corresponds to the time $t_0$ when the introduction of blood to the reagent layer 30 is detected. The graph A represents the current variation in the case where the blood amount introduced to the reagent layer 30 is sufficient, whereas the graph B represents the current variation in the case where the blood amount introduced to the reagent layer 30 is insufficient. As is clear from FIG. 6, the case where the blood amount is sufficient differs from the case where the blood amount is insufficient in current values I(−0.2) which are the values of current 0.2 second before the time $t_0$ and in current values I(0.2) which are the values of current 0.2 second after the time $t_0$. Therefore, in Step S6 and Step S7 described above, whether or not the amount of blood introduced to the reagent layer 30 is insufficient can be properly determined by the formula (1) and the formula (2) utilizing the constants a, b and c properly set based on experiments.

Figure 7:
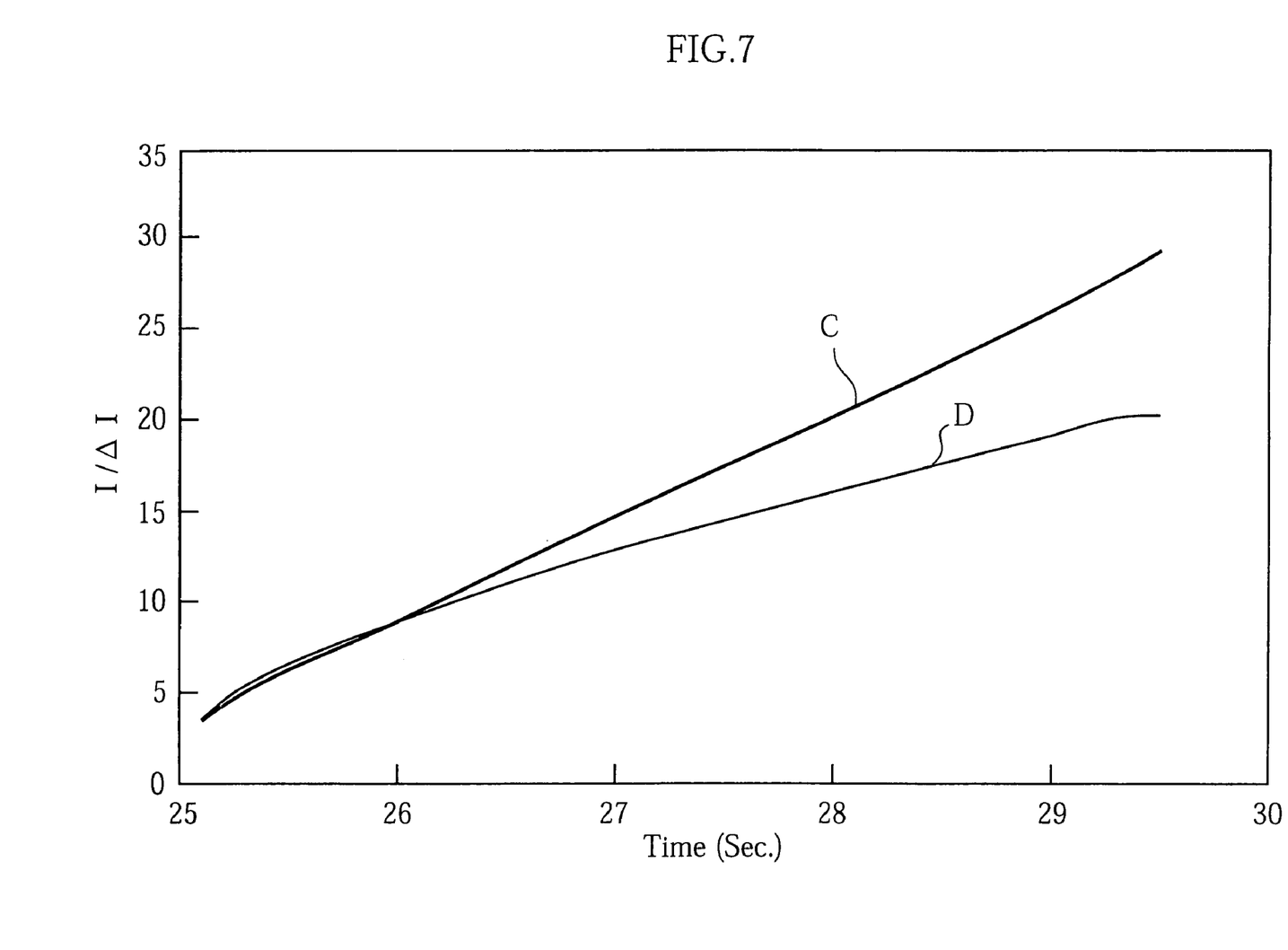
FIG. 7 shows variation with time of the value I/I after the application of voltage across the measuring electrode and the counterpart electrode is restarted.

FIG. 7 shows an example of variation with time of the value I/ΔI after the application of voltage across the measuring electrode 22 and the counterpart electrode 23 is restarted in Step S12. In FIG. 7, the abscissa represents time and the ordinate represents I/ΔI. Specifically, the abscissa represents the time which has passed from the time $t_0$ when the introduction of blood to the reagent layer 30 was detected. The graph C represents the value I/ΔI in the case where the blood amount introduced to the reagent layer 30 is sufficient, whereas the graph D represents the value I/ΔI in the case where the blood amount introduced to the reagent layer 30 is insufficient. The value I/ΔI is represented by the following formula 5. In the formula 5, I(t) is the value of current flowing between the measuring electrode 22 and the counterpart electrode 23 when t seconds has passed from the time $t_0$.

$$\frac{I}{\Delta I} = \frac{I(t)}{I(t) - I(t + 0.5)} \quad (5)$$

Figure 8:
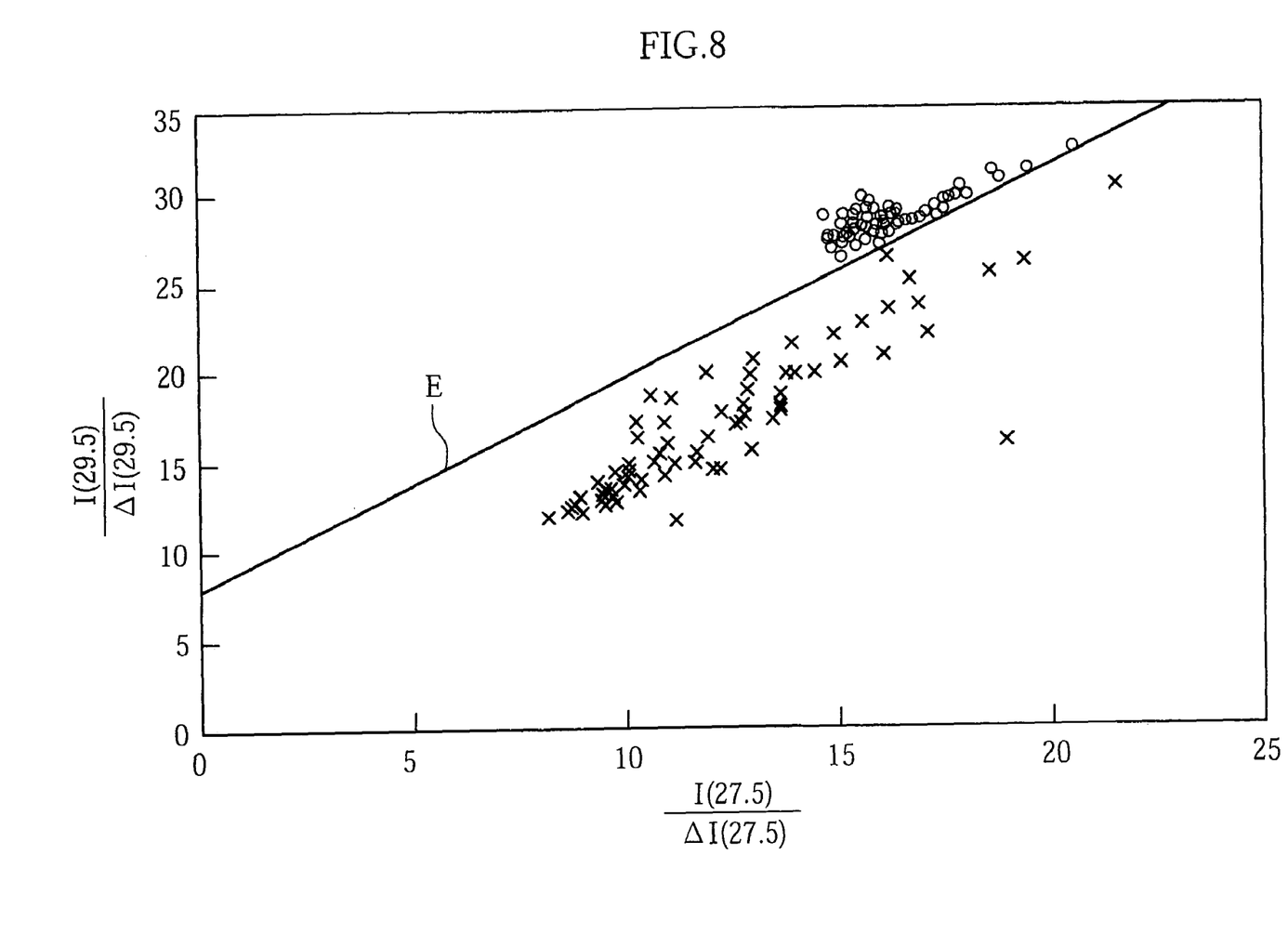
FIG. 8 shows the relationship between the value I/I and the amount of blood introduced to the reagent layer after the application of voltage across the measuring electrode and the counterpart electrode 23 restarted.

FIG. 8 shows an example of relationship between the value I/ΔI and the amount of blood introduced to the reagent layer 30 after the application of voltage across the measuring electrode 22 and the counterpart electrode 23 is restarted. In FIG. 8, the abscissa represents I(27.5)/ΔI(27.5), and the ordinate represents I(29.5)/ΔI(29.5). The marks o represent the case where the amount of blood introduced to the reagent layer 30 is sufficient, whereas the marks x represent the case where the blood amount is insufficient. As is clear from FIG. 8, with the straight line E set as the boundary, the amount of blood introduced to the reagent layer 30 is sufficient on the upper side of the straight line E, whereas the blood amount is insufficient on the lower side of the straight line E. The same result as that of FIG. 8 is obtained in the case where the abscissa represents I(25.5)/ΔI(25.5) and the ordinate represents I(27.5)/ΔI(27.5). Therefore, in Step S13 and Step S14 described above, whether or not the amount of blood introduced to the reagent layer 30 is insufficient can be properly determined by the formula (3) and the formula (4) utilizing the constants e, f and g, h properly set based on experiments.

In the quantitative analyzing method and the quantitative analyzer for realizing the method according to the present invention, whether or not the blood amount is insufficient is determined using a parameter calculated based on the current flowing between the measuring electrode 22 and the counterpart electrode 23. Therefore, by utilizing the determination, it is possible to effectively reduce erroneous measurements due to the insufficiency of blood as a sample liquid introduced to the reagent layer 30 of the sensor 21. In determining whether or not the blood amount is insufficient, the temperature detected by the temperature sensor 9 is taken into consideration so that erroneous determination due to the change of ambient temperature of the quantitative analyzer can be prevented.

After the time $t_0$ when introduction of blood to the reagent layer 30 is detected, application of a predetermined voltage is continued for one second, for example, till the time $t_1$, and whether or not the blood amount is insufficient is determined using a parameter calculated based on the current measured during that period of time. Therefore, it is possible to determine early and accurately whether or not the amount of blood introduced to the reagent layer 30 is insufficient.

The application of voltage to the reagent layer 30 is intermitted for a predetermined period of time after the introduction of blood for promoting the reaction at the reagent layer 30, and thereafter, a voltage is applied across the measuring electrode 22 and the counterpart electrode 23 for measuring the glucose concentration. Therefore, to detect the insufficiency of blood early to avoid useless measuring, it is preferable that the insufficiency of blood is accurately detected before the period of intermission of the voltage application starts. However, the current flowing between the measuring electrode 22 and the counterpart electrode 23 is small and unstable immediately after the time $t_0$, so that accurate detection of blood insufficiency is difficult if the voltage application intermission period is started at the time $t_0$ as is in the prior art quantitative analyzer. Specifically, it has been conventionally considered that, it is necessary, at the time $t_0$, to determine only whether or not the blood is introduced to the reagent layer 30, and a threshold value for the determination has been set to a sufficiently low level for shortening the total time for the analysis. Therefore, since the current flowing between the measuring electrode 22 and the counterpart electrode 23 is small and unstable at the time $t_0$, it is difficult to reliably obtain accurate determination results when the insufficiency in blood amount is determined using only the current value before the threshold value is reached.

In this embodiment, however, the application of voltage across the measuring electrode 22 and the counterpart electrode 23 is continued until the time $t_1$ after significant time has passed from the time $t_0$, and during that period of time, sufficiency or insufficiency of blood is determined using a parameter calculated based on the current flowing between the measuring electrode 22 and the counterpart electrode 23, thereby preventing erroneous determination.

In this embodiment, two times of determination of Steps S6 and S7, and two times of determination of Steps S13 and S14 are performed. The amount of blood introduced to the reagent layer 30 is finally determined to be insufficient only when the blood amount is judged as insufficient in both of the two times of determination. Therefore, it is possible to reliably prevent the blood amount from being erroneously determined as insufficient, though sufficient, due to the instability of current flowing between the measuring electrode 22 and the counterpart electrode 23.

In this embodiment, whether or not the blood amount is insufficient is determined before and after the intermission period of voltage application to the measuring electrode 22 and the counterpart electrode 23. Thus, the determination before the voltage application intermission period prevents waste of measuring time. Further, the determination after the voltage application intermission period prevents the blood amount from being finally determined as sufficient by mistake though in fact insufficient.

An experiment was performed using the above-described quantitative analyzer under the conditions described below.

As sample liquid, three aqueous solutions of glucose which differ from each other in concentration were used instead of blood. The glucose solution of the lower concentration contained 54 mg/dL of glucose, 1 g/L of benzoic acid, and 0.1 g/L of Acid Red. The glucose solution of the medium concentration contained 86 mg/dL of glucose, 1 g/L of benzoic acid, and 0.1 g/L of Acid Red. The glucose solution of the higher concentration contained 286 mg/dL of glucose, 1 g/L of benzoic acid, and 0.1 g/L of Acid Red. The excitation pattern of voltage applied across the measuring electrode 22 and the counterpart electrode 23, parameters calculated based on measured current, and calculation formulae for the determination using the parameters used were as those in the above-described embodiment. In the experiment, fifty sensors 21 were used for each of the glucose solutions, i.e. that of the lower concentration, that of the medium concentration, and that of the higher concentration. Among the fifty sensors for each glucose solution, an insufficient amount of glucose solution was supplied to twenty-five sensors and a sufficient amount of glucose solution was supplied to the remaining twenty-five sensors. Herein, the insufficient amount is 1.2-1.5 μL and the sufficient amount is 2 μL.

Figure 9:
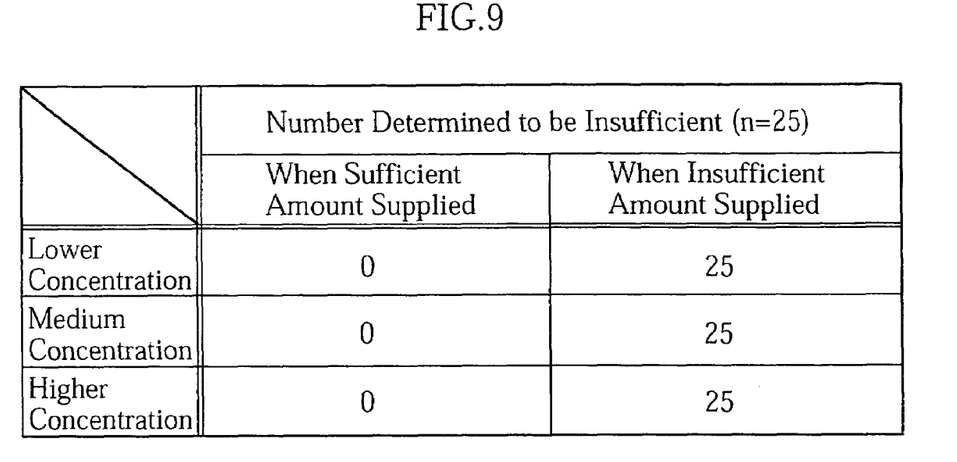
FIG. 9 shows the experimental results using the quantitative analyzer shown in FIG. 1.

FIG. 9 shows the experimental results under such conditions. Regardless of the difference in glucose concentration, the probability that the blood amount was finally determined to be insufficient when an insufficient amount was supplied was 100%, and the probability that the blood amount was finally determined to be insufficient when a sufficient amount was supplied was 0%. Thus, regardless of the difference in glucose concentration, erroneous determination was not made.

In the present invention, as a parameter for determining whether or not the amount of blood introduced to the reagent layer 30 is insufficient, use may be made of a differentiation dI/dt of current instead of the value of current flowing between the measuring electrode 22 and the counter part electrode 23 or the difference I of current at a predetermined time. Although whether or not the blood amount is insufficient is determined based on two values of current measured at different times in the above-described embodiment, such determination may be made based on a single current value measured at a predetermined time. In the above-described embodiment, the blood amount is finally determined to be insufficient only when two times of determining performed successively indicate that the blood amount is insufficient. However, the blood amount may be finally determined to be insufficient when a single time of determining indicates that it is insufficient. Alternatively, such determining may be performed successively three or more times and the blood amount may be finally determined to be insufficient only when the three or more times of determining indicate that the blood amount is insufficient. Although whether or not the blood amount is insufficient is determined before and after the period during which the application of voltage across the measuring electrode 22 and the counterpart electrode 23 is intermitted in the above-described embodiment, such determining may be performed either before or after the period. In the above-described embodiment, whether or not the blood amount is insufficient is determined before and after the time $t_0$ before the intermission period of voltage application. However, such determining may be made either before or after the time $t_0$. Further, although the voltage application across the measuring electrode 22 and the counterpart electrode 23 is intermitted during the operation of the second timer, a low voltage, which does not substantially cause current to flow between the electrodes, may be continuously applied. Although a potential step method is utilized in the embodiment, the present invention is not limited to the potential step method. Further, although reference is made of the case in which the sample liquid is blood and the substance to be measure is glucose in the embodiment, the present invention is not limited thereto. In the embodiment, detection of the insufficiency of sample liquid is described. However, when insufficiency is detected although a sufficient amount of sample liquid is supplied, it is considered that the hematocrit or viscosity of the sample liquid is high. Such conditions as hematocrit or viscosity of the sample liquid can be measured by the present invention.

The invention claimed is:

1. A quantitative analyzing method for electrochemically measuring concentration of a substance in a sample liquid using a sensor including a reagent layer which contains a reagent for reacting with the substance and to which the sample' liquid is introduced, and a first and a second electrodes for applying a voltage to the reagent layer, the method comprising:
   a current measuring step for applying a voltage across the first electrode and the second electrode for measuring current flowing between the first electrode and the second electrode;
   a parameter calculating step for calculating a parameter based on the measured current; and
   a determining step for determining whether or not the sample liquid introduced to the reagent layer is insufficient in amount based on the parameter and at least one predetermined constant.

2. The quantitative analyzing method according to claim 1, wherein the parameter includes a current value of the current flowing between the first electrode and the second electrode at a predetermined point of time.

3. The quantitative analyzing method according to claim 1, wherein the parameter includes a difference between a first current value at a first predetermined point of time and a second current value at a second predetermined point of time of the current flowing between the first electrode and the second electrode.

4. The quantitative analyzing method according to claim 1, wherein the parameter includes a differentiation of the current flowing between the first electrode and the second electrode at a predetermined point of time.

5. The quantitative analyzing method according to claim 1, wherein the parameter includes a third difference between a first value and a second value with respect to the current flowing between the first electrode and the second electrode, the first value being obtained by dividing a current value at a third predetermined point of time by a first difference between a current value at a first predetermined point of time and a current value at a second predetermined point of time, the third point of time being included in a period between the first point of time and the second point of, the second value being obtained by dividing a current value at a sixth predetermined point of time by a second difference between a current value at a fourth predetermined point of time and a current value at a fifth predetermined point of time, the sixth point of time being included in a period between the fourth point of time and the fifth point of time.

6. The quantitative analyzing method according to claim 1, wherein a series of process steps including the current measuring step, the parameter calculating step and the determining step is repeated a plurality of times, the sample liquid introduced to the reagent layer being finally determined to be insufficient in amount when the sample liquid is determined to be insufficient in every determining step.

7. The quantitative analyzing method according to claim 6, wherein the series of process steps including the current measuring step, the parameter calculating step and the determining step is repeated an optional number of times after the sample liquid is introduced to the reagent layer and before and/or after a second period during which current is not substantially caused to flow between the first electrode and the second electrode.

8. The quantitative analyzing method according to claim 1, wherein the current measuring step is continued for a first period from before to after a point of time when the introduction of the sample liquid to the reagent layer is detected based on the current flowing between the first electrode and the second electrode, at least a part of the parameter being calculated based on the current measured in the first period.

9. The quantitative analyzing method according to claim 1, wherein at least part of said at least one constant is varied depending on a temperature of the sample liquid.

10. A quantitative analyzer for electrochemically measuring concentration of a substance in a sample liquid using a sensor including a reagent layer which contains a reagent for reacting with the substance and to which the sample liquid is introduced, and a first and a second electrodes for applying a voltage to the reagent layer, comprising;
   voltage applying means for applying a voltage across the first electrode and the second electrode;
   current measuring means for measuring current flowing between the first electrode and the second electrode;
   calculating means for calculating a parameter based on the measurement obtained by the current measuring means; and
   determining means for determining whether or not the sample liquid introduced to the reagent layer is insufficient in amount based on the parameter calculated by the calculating means and at least one predetermined constant.

11. The quantitative analyzer according to claim 10, wherein the calculating means calculates a current value of the current flowing between the first electrode and the second electrode at a predetermined point of time as at least a part of the parameter.

12. The quantitative analyzer according to claim 10, wherein the calculating means calculates a difference between a current value at a first predetermined point of time and a current value at a second predetermined point of time of the current flowing between the first electrode and the second electrode as at least a part of the parameter.

13. The quantitative analyzer according to claim 10, wherein the calculating means calculates a differentiation of the current flowing between the first electrode and the second electrode at a predetermined point of time as at least a part of the parameter.

14. The quantitative analyzer according to claim 10, wherein the calculating means calculates, as at least a part of the parameter, a third difference between a first value and a second value with respect to the current flowing between the first electrode and the second electrode, the first value being obtained by dividing a current value at a third predetermined point of time by a first difference between a current value at a first predetermined point of time and a current value at a second predetermined point of time, the third point of time being included in a period between the first point of time and the second point of time, the second value being obtained by dividing a current value at a sixth predetermined point of time by a second difference between a current value at a fourth predetermined point of time and a current value at a fifth predetermined point of time, the sixth point of time being included in a period between the fourth point of time and the fifth point of time.

15. The quantitative analyzer according to claim 10, wherein a combination of operations performed by the current measuring means, the calculating means and the determining means is repeated a plurality of times, the sample liquid introduced to the reagent layer being finally determined to be insufficient in amount when the determining means determines that the sample liquid is insufficient at every repetition of the combined operations.

16. The quantitative analyzer according to claim 10, wherein the current measuring means operates for a first period from before to after a point of time when the introduction of the sample liquid to the reagent layer is detected based on the current flowing between the first electrode and the second electrode, the calculating means calculating at least a part of the parameter based on the current measured in the first period.

17. The quantitative analyzer according to claim 10, wherein a combination of operations performed by the current measuring means, the calculating means and the determining means is repeated an optional number of times after the sample liquid is introduced to the reagent layer and before and/or after a second period during which current is not substantially caused to flow between the first electrode and the second electrode.

18. The quantitative analyzer according to claim 17, wherein the determining means varies at least part of said at least one constant depending on a temperature of the sample liquid.

19. A quantitative analyzing method for electrochemically measuring concentration of a substance in a sample liquid using a sensor including a reagent layer which contains a reagent for reacting with the substance and to which the sample liquid is introduced, and a first and a second electrodes for applying a voltage to the reagent layer, the method comprising:

a first current measuring step for applying a voltage across the first electrode and the second electrode for a first period for measuring current flowing between the first electrode and the second electrode;

a sample liquid introducing step for introducing the sample liquid to the reagent layer within the first period;

a first parameter calculating step for calculating a parameter based on the current measured in the first current measuring step;

a first determining step for determining whether or not the sample liquid introduced to the reagent layer is insufficient in amount based on the parameter obtained in the first parameter calculating step and at least one first constant determined in advance;

a reaction promoting step for substantially intermitting voltage application across the first electrode and the second electrode for a second period;

a second current measuring step for applying a voltage across the first electrode and the second electrode for a third period for measuring current flowing between the first electrode and the second electrode;

a second parameter calculating step for calculating a parameter based on the current measured in the second current measuring step; and a second determining step for determining whether or not the sample liquid introduced to the reagent layer is insufficient in amount based on the parameter obtained in the second parameter calculating step and at least one second constant determined in advance.

20. The quantitative analyzing method according to claim 19, wherein a first series of process steps including the first current measuring step, the first parameter calculating step and the first determining step and/or a second series of process steps including the second current measuring step, the second parameter calculating step and the second determining step are repeated respectively a plurality of times, the sample liquid introduced to the reagent layer being finally determined to be insufficient in amount when the sample liquid is determined to be insufficient in every first determining step in the first series of process steps or in every second determining step in the second series of process steps.

* * * * *